(12) United States Patent
Kawano et al.

(10) Patent No.: US 7,148,055 B2
(45) Date of Patent: Dec. 12, 2006

(54) PROCESS FOR PRODUCTION OF OPTICALLY ACTIVE 3-HYDROXYPENTANENITRILE

(75) Inventors: Shigeru Kawano, Takasago (JP); Yoshihiko Yasohara, Takasago (JP)

(73) Assignee: Kaneka Corporation, Osaka (JP)

( * ) Notice: Subject to any disclaimer, the term of this patent is extended or adjusted under 35 U.S.C. 154(b) by 391 days.

(21) Appl. No.: 10/491,115

(22) PCT Filed: Oct. 3, 2002

(86) PCT No.: PCT/JP02/10312

§ 371 (c)(1),
(2), (4) Date: Mar. 26, 2004

(87) PCT Pub. No.: WO03/031636

PCT Pub. Date: Apr. 17, 2003

(65) Prior Publication Data

US 2004/0235124 A1 Nov. 25, 2004

(30) Foreign Application Priority Data

Oct. 5, 2001 (JP) ............................. 2001-309682

(51) Int. Cl.
*C12P 41/00* (2006.01)
(52) U.S. Cl. ..................................... 435/280
(58) Field of Classification Search ............... None
See application file for complete search history.

(56) References Cited

FOREIGN PATENT DOCUMENTS

WO  WO 94/21617 A1  9/1994
WO  WO 2005/044973 A2  5/2005

OTHER PUBLICATIONS

Hackler, R.E., et al., "The Syntheses of 5-Amino-3-*t*-butylisothiazole and 3-Amino-5-*t*-butylisothiazole," *Journal of Heterocyclic Chemistry*, vol. 26, No. 6, 1989, pp. 1575-1578.

Kiljunen, E., et al., "Novel (R)-Oxynitrilase Sources for the Synthesis of (R)-Cyanohydrins in Diisopropyl Ether," *Tetrahedron: Asymmetry*, vol. 8, No. 8, Apr 24, 1997, pp. 1225-1234.

Effenberger, F., et al., "Enantioselektive Veresterung Racemisher Cyanhydrine und Enantioselektive Hydrolyse Oder Umesterung Racemisher Cyanhydrine und Enantioselektive Hydrolyse Oder Umesterung Racemischer Cyanhydrinester Mittels Lipasen," *Liebigs Annalen Der Chemie*, No. 1, 1991, pp. 47-54.

Supplementary Partial European Search Report from Application No. EP 02 80 0753, Oct. 27, 2005, 6 pages.

Itoh, Toshiyuki et al., "Thiacrown Ether Technology in Lipase-Catalyzed Reaction: Scope and Limitation for Preparing Optically Active 3-Hydroxyalkanenitriles and Application to Insect Pheromone Synthesis," *J. Org. Chem.*, vol. 62, No. 26, 1997, pp. 9165-9172.

International Search Report From Corresponding International Application No. PCT/JP02/10312, Dated Jan. 28, 2003, 3 Pages.

*Primary Examiner*—Sandra E. Saucier
(74) *Attorney, Agent, or Firm*—Brinks Hofer Gilson & Lione

(57) ABSTRACT

The present invention provides a method for preparing optically active 3-hydroxypentanenitrile with high yield. Optically active 3-hydroxypentanenitrile is prepared by stereoselectively reducing 3-ketopentanenitrile by action of an enzyme, which asymmetrically reduces 3-ketopentanenitrile to optically active 3-hydroxypentanenitrile. Also, alkali metal salt of 3-ketopentanenitrile, which is a stable compound without problems regarding storage, can be efficiently obtained.

7 Claims, No Drawings

PROCESS FOR PRODUCTION OF OPTICALLY ACTIVE 3-HYDROXYPENTANENITRILE

RELATED APPLICATIONS

This application is a nationalization of PCT Application No. PCT/JP02/10312 filed Oct. 3, 2002. This application claims priority from Japanese Patent Application No. 2001-309682 filed on Oct. 5, 2001.

TECHNICAL FIELD

The present invention relates to a process for preparing optically active 3-hydroxypentanenitrile. Optically active 3-hydroxypentanenitrile is a compound that is useful as a synthetic raw material and an intermediate of pharmaceutical products or agricultural chemicals, which require optical activity.

BACKGROUND ART

As a process for preparing optically active 3-hydroxypentanenitrile, known is the optical resolution method (J. Org. Chem., 62, 9165 (1997)), wherein 3-acetoxynitrile compound which is a racemic body is hydrolyzed in the presence of thio-crown ether using a lipase derived from *Pseudomonas cepacia*. However, because this method is an optical resolution method, the yield of one enantiomer is low, that is at most 50%, and therefore is not satisfactory. Also, because the optical purity of the produced 3-hydroxypentanenitrile is low and thio-crown ether is added to improve the discrimination of an enzyme, industrial operation is difficult when considering cost and safety.

Also, a method for synthesizing 3-ketopentanenitrile, which is used as a raw material for preparing optically active 3-hydroxypentanenitrile in the present invention, is already known (WO94/21617). However, the obtained 3-ketopentanenitrile is known to be an unstable compound and to polymerize on its own (Aust. J. Chem., 44, 1263, (1991)). Therefore, 3-ketopentanenitrile is difficult to store over a long period of time and difficult to use from an industrial viewpoint.

As a result of intensive studies to develop an efficient process for preparing optically active 3-hydroxypentanenitrile, the present inventors have newly discovered an enzyme source, which has ability to stereoselectively reduce and convert 3-ketopentanenitrile into optically active 3-hydroxypentanenitrile. Thus, the present invention was achieved.

Furthermore, as a result of studies focusing on alkali metal salt of 3-ketopentanenitrile in order to avoid problems regarding storage due to unstableness of 3-ketopentanenitrile, a process for efficiently obtaining alkali metal salt of 3-ketopentanenitrile, which is a stable compound without problems regarding storage, has been discovered. Thus, the present invention was achieved.

DISCLOSURE OF INVENTION

That is, the present invention relates to a process for preparing optically active 3-hydroxypentanenitrile represented by the following formula (1):

wherein an enzyme, which asymmetrically reduces 3-ketopentanenitrile to optically active 3-hydroxypentanenitrile, acts upon 3-ketopentanenitrile represented by the following formula (2):

to obtain optically active 3-hydroxypentanenitrile.

The enzyme is preferably an enzyme present in a cell, a culture solution or a treated substance thereof of a microorganism selected from the group consisting of *Arthroascus* genus, *Candida* genus, *Cryptococcus* genus, *Debaromyces* genus, *Dekkera* genus, *Dipodascus* genus, *Geotrichum* genus, *Guilliermondella* genus, *Hyphopichia* genus, *Issatchenkia* genus, *Kluyveromyces* genus, *Komagataella* genus, *Lipomyces* genus, *Lodderomyces* genus, *Metschnikowia* genus, *Ogataea* genus, *Pichia* genus, *Rhodotorula* genus, *Rhodsporidium* genus, *Schizoblastosporion* genus, *Schwanniomyces* genus, *Stephanoascus* genus, *Torulaspora* genus, *Trichosporon* genus, *Williopsis* genus, *Yarrowia* genus, *Acidephilium* genus, *Agrobacterium* genus, *Alcaligenes* genus, *Arthrobacter* genus, *Brevundimonas* genus, *Cellulomonas* genus, *Comamonas* genus, *Microbacterium* genus, *Paenibacillus* genus, *Rhodococcus* genus, *Citeromyces* genus, *Achromobacter* genus, *Corynebacterium* genus, *Devosia* genus, *Hofnia* genus, *Proteus* genus, *Providencia* genus, *Pseudomonas* genus, *Absidia* genus, *Aegerita* genus, *Agrocybe* genus, *Amylostereum* genus, *Aspergillus* genus, *Corynascucs* genus, *Dendryphiella* genus, *Emericella* genus, *Fusarium* genus, *Gibberella* genus, *Glomerella* genus, *Macrophoma* genus, *Micronectriella* genus, *Mortierella* genus, *Mucor* genus, *Nannizzia* genus, *Penicillium* genus, *Phialophora* genus, *Rhizopus* genus, *Sclerotinia* genus, *Sclerotium* genus and *Streptomyces* genus; and/or a purified enzyme obtained from the microorganism.

The absolute configuration of the produced optically active 3-hydroxypentanenitrile is preferably R-configuration and the enzyme is preferably an enzyme present in a cell, a culture solution or a treated substance thereof of a microorganism selected from the group consisting of *Arthroascus* genus, *Candida* genus, *Cryptococcus* genus, *Debaryomyces* genus, *Dekkera* genus, *Geotrichum* genus, *Guilliermondella* genus, *Issatchenkia* genus, *Kluyveromyces* genus, *Komagataella* genus, *Lipomyces* genus, *Lodderomyces* genus, *Metschnikowia* genus, *Ogataea* genus, *Pichia* genus, *Rhodotorula* genus, *Rhodsporidium* genus, *Schwanniomyces* genus, *Stephanoascus* genus, *Torulaspora* genus, *Trichosporon* genus, *Williopsis* genus, *Yarrowia* genus, *Acidephilium* genus, *Agrobacterium* genus, *Alcaligenes* genus, *Arthrobacter* genus, *Cellulomonas* genus, *Comamonas* genus, *Microbacterium* genus, *Rhodococcus* genus, *Citeromyces* genus, *Achromobacter* genus, *Corynebacterium* genus, *Devosia* genus, *Hofnia* genus, *Proteus* genus, *Providencia* genus, *Absidia* genus, *Aegerita* genus, *Agrocybe* genus, *Amylostereum* genus, *Aspergillus* genus, *Corynascucs* genus, *Dendryphiella* genus, *Emericella* genus, *Fusarium* genus, *Gibberella* genus, *Glomerella* genus, *Macrophoma* genus, *Micronectriella* genus, *Mortierella* genus, *Mucor* genus, *Nannizzia* genus, *Penicillium* genus, *Phialophor* genus, *Rhizopus* genus, *Sclerotinia* genus, *Sclerotium* genus and *Streptomyces* genus; and/or a purified enzyme obtained from the microorganism.

The absolute configuration of the produced optically active 3-hydroxypentanenitrile is preferably R-configuration and the enzyme is preferably an enzyme present in a cell, a culture solution or a treated substance thereof of a microorganism selected from the group consisting of *Arthroascus javanensis, Candida cantarellii, Candida fennica, Candida glabrata, Candida gropengiesseri, Candida, Candida maris, Candida melinii, Candida musae, Candida pararugosa, Candida pinus, Candida sorbophila, Candida tenuis, Candida utilis, Cryptococcus curvatus, Cryptococcus humicolus, Debaryomyces hansenii, Debaryomyces hansenii* var. *fabryi, Debaryomyces hansenii* var. *hansenii, Debaryomyces marama, Debaryomyces nepalensis, Dekkera anomala, Geotrichum candidum, Geotrichum eriense, Geotrichum fermentans, Guilliermondella selenospora, Issatchenkia orientalis, Issatchenkia terricola, Kluyveromyces marxianus, Komagataella pastoris, Lipomyces starkeyi, Lodderomyces elongisporus, Metschnikowia bicuspidata, Metschnikowia gruessii, Ogataea pini, Ogataea wickerhamii, Pichia anomala, Pichia canadensis, Pichia jadinii, Pichia petersonii, Pichia rhodanensis, Pichia silvicola, Pichia triangularis, Rhodotorula lactosa, Rhodotorula rubra, Rhodsporidium diobovatum, Rhodsporidium sphaerocarpum, Rhodsporidium toruloides, Schwanniomyces occidentalis* var. *occidentalis, Stephanoascus ciferrii, Toruplaspora delbrueckii, Trichosporon cutaneum, Williopsis saturnus* var. *mrakii, Williopsis saturnus* var. *saturnus, Williopsis saturnus* var. *suaveolens, Yarrowia lipolytica, Acidephilium cryptum, Agrobacterium tumefacience, Alcaligenes* sp., *Achromobacter xylosoxidans* subsp. *denitrificans, Arthrobacter protophomiae, Cellulomonas gelida, Comamonas testosteroni, Microbacterium arborescens, Rhodococcus equi, Rhodococcus erythropolis, Rhodococcus rhodochrous, Candida magnoliae, Citeromyces matritensis, Pichia bispora, Trichosporon loubieri* var. *loubieri, Corynebacterium ammoniagenes, Corynebacterium flavescens, Devosia riboflavina, Hofnia alvei, Proteus vulgaris, Providencia alcalifaciens, Absidia coerulea, Absidia hyalospora, Aegerita candida, Agrocybe cylindracea, Amylostereum areolatum, Aspergillus niger, Aspergillus phoenicis, Aspergillus sojae, Corynascucs sepedonium, Dendryphiella salina, Emericella nidulans* var. *nidulans, Emericella unguis, Fusarium oxysporum, Fusarium anguioides, Gibberella fujikuroi, Glomerella cingulata, Macrophoma commelinae, Micronectriella cucumeris, Mortierella isabellina, Mortierella ramanniana* var. *angulispora, Mucor tuberculisporus, Mucor inaequisporus, Nannizzia gypsea* var. *incurvata, Penicillium chermesium, Penicillium expansum, Phialophora fastigiata, Rhizopus niveus, Rhizopus oryzae, Sclerotinia sclerotiorum, Sclerotium delphinii, Streptomyces cacaoi* subsp. *asoensis* and *Streptomyces* sp.; and/or a purified enzyme obtained from the microorganism.

The absolute configuration of the produced optically active 3-hydroxypentanenitrile is preferably S-configuration and the enzyme is preferably an enzyme present in a cell, a culture solution or a treated substance thereof of a microorganism selected from the group consisting of *Candida* genus, *Dipodascus* genus, *Geotrichum* genus, *Hyphopichia* genus, *Kluyveromyces* genus, *Pichia* genus, *Schizoblas-* *tosporion* genus, *Schwanniomyces* genus, *Brevundimonas* genus, *Paenibacillus* genus, *Rhodotorula* genus, *Pseudomonas* genus and *Streptomyces* genus; and/or a purified enzyme obtained from the microorganism.

The absolute configuration of the produced optically active 3-hydroxypentanenitrile is preferably S-configuration and the enzyme is preferably an enzyme present in a cell, a culture solution or a treated substance thereof of a microorganism selected from the group consisting of *Candida albicans, Candida haemulonii, Candida intermedia, Candida maltosa, Candida mogii, Candida oleophila, Dipodascus ovetensis, Dipodascus tetrasperma, Geotrichum fragrans, Hypopichia burtonii, Kluyveromyces polysporus, Pichia stipitis, Schizoblastosporion kobayasii, Schwanniomyces occidentalis* var. *occidentalis, Brevundimonas diminuta, Paenibacillus alvei, Rhodotorula glutinis* var. *dairenensis, Pseudomonas stutzeri, Pseudomonas mendocina, Streptomyces coelescens* and *Streptomyces hydrogenans*; and/or a purified enzyme obtained from the microorganism.

Either or both of oxidized nicotinamide adenine dinucleotide ($NAD^+$) and oxidized nicotinamide adenine dinucleotide phosphate ($NADP^+$) preferably coexists with an enzyme that reduces each to a reduced form and a substrate for reducing.

An alkali metal salt of 3-ketopentanenitrile represented by the following formula (3):

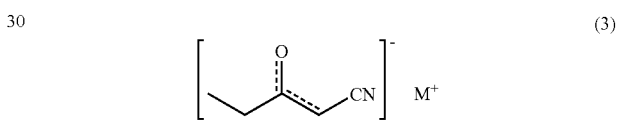

(wherein M represents an alkali metal) is preferably used as 3-ketopentanenitrile.

The present invention also relates to a process for preparing an alkali metal salt of 3-ketopentanenitrile, which comprises synthesizing 3-ketopentanenitrile from propionic acid ester and acetonitirle in the presence of an alkali metal base; and obtaining 3-ketopentanenitrile from the reaction system as an alkali metal salt represented by the following formula (3):

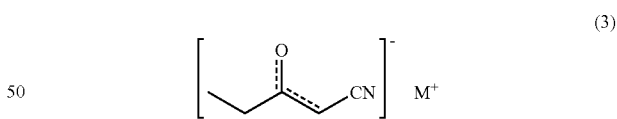

(wherein M represents an alkali metal).

BEST MODE FOR CARRYING OUT THE INVENTION

The present invention is described below.

The 3-ketopentanenitrile used as the substrate of the present invention can be synthesized by the method described in WO94/21617.

The enzyme used in the present invention is an enzyme that converts 3-ketopentanenitrile into optically active 3-hydroxypentanenitrile. Specifically, examples are reductase and dehydrogenase, which reduce a carbonyl group into a hydroxyl group. These enzymes are present in a cell, a culture solution or a treated substance of the cell or are purified and in the present invention, these may be used alone or in a combination of two or more kinds.

A microorganism having ability to convert 3-ketopentanenitrile into optically active 3-hydroxypentanenitrile can be found, for example, from the method described below. A test tube is charged with 5 ml of a liquid medium (pH 7) comprising 40 g of glucose, 3 g of yeast extract, 6.5 g of diammonium hydrogenphosphate, 1 g of potassium dihydrogenphosphate, 0.8 g of magnesium sulfate heptahydrate, 60 mg of zinc sulfate heptahydrate, 90 mg of iron sulfate heptahydrate, 5 mg of copper sulfate pentahydrate, 10 mg of manganese sulfate tetrahydrate and 100 mg of sodium chloride (all per 1 L) and sterilized. Then, the microorganism is aseptically inoculated and cultured by shaking at 30° C. for 2 to 3 days. Subsequently, the cells are collected by centrifugation and suspended in 1 to 5 ml of a phosphate buffer solution containing 2 to 10% of glucose. The suspension is added to a test tube in which 2.5 to 25 mg of 3-ketopentanenitrile is added in advance and shaken for 2 to 3 days at 30° C. At this time, a substance obtained by drying the centrifugalized cells in a desiccator or by acetone can also be used.

The microorganism used in the present invention can be any microorganism, as long as the microorganism has ability to convert 3-ketopentanenitrile into optically active 3-hydroxypentanenitrile. Examples are microorganisms belonging to *Arthroascus* genus, *Candida* genus, *Cryptococcus* genus, *Debaryomyces* genus, *Dekkera* genus, *Dipodascus* genus, *Geotrichum* genus, *Guilliermondella* genus, *Hyphopichia* genus, *Issatchenkia* genus, *Kluyveromyces* genus, *Komagataella* genus, *Lipomyces* genus, *Lodderomyces* genus, *Metschnikowia* genus, *Ogataea* genus, *Pichia* genus, *Rhodotorula* genus, *Rhodsporidium* genus, *Schizoblastosporion* genus, *Schwanniomyces* genus, *Stephanoascus* genus, *Torulaspora* genus, *Trichosporon* genus, *Williopsis* genus, *Yarrowia* genus, *Acidephilium* genus, *Agrobacterium* genus, *Alcaligenes* genus, *Arthrobacter* genus, *Brevundimonas* genus, *Cellulomonas* genus, *Comamonas* genus, *Microbacterium* genus, *Paenibacillus* genus, *Rhodococcus* genus, *Citeromyces* genus, *Achromobacter* genus, *Corynebacterium* genus, *Devosia* genus, *Hofnia* genus, *Proteus* genus, *Providencia* genus, *Pseudomonas* genus, *Absidia* genus, *Aegerita* genus, *Agrocybe* genus, *Amylostereum* genus, *Aspergillus* genus, *Corynascucs* genus, *Dendryphiella* genus, *Emericella* genus, *Fusarium* genus, *Gibberella* genus, *Glomerella* genus, *Macrophoma* genus, *Micronectriella* genus, *Mortierella* genus, *Mucor* genus, *Nannizzia* genus, *Penicillium* genus, *Phialophora* genus, *Rhizopus* genus, *Sclerotinia* genus, *Sclerotium* genus and *Streptomyces* genus.

Particularly, when converting into 3-hydroxypentanenitrile whose absolute configuration is R-configuration, preferable microorganisms are microorganisms belonging to *Arthroascus* genus, *Candida* genus, *Cryptococcus* genus, *Debaryomyces* genus, *Dekkera* genus, *Geotrichum* genus, *Guilliermondella* genus, *Issatchenkia* genus, *Kluyveromyces* genus, *Komagataella* genus, *Lipomyces* genus, *Lodderomyces* genus, *Metschnikowia* genus, *Ogataea* genus, *Pichia* genus, *Rhodotorula* genus, *Rhodsporidium* genus, *Schwanniomyces* genus, *Stephanoascus* genus, *Torulaspora* genus, *Trichosporon* genus, *Williopsis* genus, *Yarrowia* genus, *Acidephilium* genus, *Agrobacterium* genus, *Alcaligenes* genus, *Arthrobacter* genus, *Cellulomonas* genus, *Comamonas* genus, *Microbacterium* genus, *Rhodococcus* genus, *Citeromyces* genus, *Achromobacter* genus, *Corynebacterium* genus, *Devosia* genus, *Hofnia* genus, *Proteus* genus, *Providencia* genus, *Absidia* genus, *Aegerita* genus, *Agrocybe* genus, *Amylostereum* genus, *Aspergillus* genus, *Corynascucs* genus, *Dendryphiella* genus, *Emericella* genus, *Fusarium* genus, *Gibberella* genus, *Glomerella* genus, *Macrophoma* genus, *Micronectriella* genus, *Mortierella* genus, *Mucor* genus, *Nannizzia* genus, *Penicillium* genus, *Phialophora* genus, *Rhizopus* genus, *Sclerotinia* genus, *Sclerotium* genus and *Streptomyces* genus. Further preferable examples are *Arthroascus javanensis, Candida cantarellii, Candida fennica, Candida glabrata, Candida gropengiesseri, Candida keyr, Candida maris, Candida melinii, Candida musae, Candida pararugosa, Candida pinus, Candida sorbophila, Candida tenuis, Candida utilis, Cryptococcus curvatus, Cryptococcus humicolus, Debaryomyces hansenii, Debaryomyces hansenii* var. *fabryi, Debaryomyces hansenii* var. *hansenii, Debaryomyces marama, Debaryomyces nepalensis, Dekkera anomala, Geotrichum candidum, Geotrichum eriense, Geotrichum fermentans, Guilliermondella selenospora, Issatchenkia orientalis, Issatchenkia terricola, Kluyveromyces marxianus, Komagataella pastoris, Lipomyces starkeyi, Lodderomyces elongisporus, Metschnikowia bicuspidata, Metschnikowia gruessii, Ogataea pini, Ogataea wickerhamii, Pichia anomala, Pichia canadensis, Pichia jadinii, Pichia petersonii, Pichia rhodanensis, Pichia silvicola, Pichia triangularis, Rhodotorula lactosa, Rhodotorula rubra, Rhodsporidium diobovatum, Rhodsporidium sphaerocarpum, Rhodsporidium toruloides, Schwanniomyces occidentalis* var. *occidentalis, Stephanoascus ciferrii, Torulaspora delbrueckii, Trichosporon cutaneum, Williopsis saturnus* var. *mrakii, Williopsis saturnus* var. *saturnus, Williopsis saturnus* var. *suaveolens, Yarrowia lipolytica, Acidephilium cryptum, Agrobacterium tumefacience, Alcaligenes* sp., *Achromobacter xylosoxidans* subsp. *denitrificans, Arthrobacter protophormiae, Cellulomonas gelida, Comamonas testosteroni, Microbacterium arborescens, Rhodococcus equi, Rhodococcus erythropolis, Rhodococcus rhodochrous, Candida magnoliae, Citeromyces matritensis, Pichia bispora, Trichosporon loubieri* var. *loubieri, Corynebacterium ammoniagenes, Corynebacterium flavescens, Devosia riboflavina, Hofnia alvei, Proteus vulgaris, Providencia alcalifaciens, Absidia coerulea, Absidia hyalospora, Aegerita candida, Agrocybe cylyndracea, Amylostereum areolatum, Aspergillus niger, Aspergillus phoenicis, Aspergillus sojae, Corynascucs sepedonium, Dendryphiella salina, Emericella nidulans* var. *nidulans, Emericella unguis, Fusarium oxysporum, Fusarium anguioides, Gibberella fujikuroi, Glomerella cingulata, Macrophoma commelinae, Micronectriella cucumeris, Mortierella isabellina, Mortierella ramanniana* var. *angulispora, Mucor tuberculisporus, Mucor inaequisporus, Nannizzia gypsea* var. *incurvata, Penicillium chermesium, Penicillium expansum, Phialophora fastigiata, Rhizopus niveus, Rhizopus oryzae, Sclerotinia sclerotiorum, Sclerotium delphinii, Streptomyces cacaoi* subsp. *asoensis* and *Streptomyces* sp.

When converting into 3-hydroxypentanenitrile whose absolute configuration is S-configuration, preferable microorganisms are microorganisms belonging to *Candida* genus, *Dipodascus* genus, *Geotrichum* genus, *Hyphopichia* genus, *Kluyveromyces* genus, *Pichia* genus, *Schizoblastosporion* genus, *Schwanniomyces* genus, *Brevundimonas* genus, *Paenibacillus* genus, *Rhodotorula* genus, *Pseudomonas* genus and *Streptomyces* genus. Further preferable examples are *Candida albicans, Candida haemulonii, Candida intermedia, Candida maltosa, Candida mogii, Candida oleophila, Dipodascus ovetensis, Dipodascus tetrasperma, Geotrichum fragrans, Hypopichia burtonii, Kluyveromyces polysporus, Pichia stipitis, Schizoblastosporion kobayasii, Schwanniomyces occidentalis* var. *occidentalis, Brevundimonas diminuta, Paenibacillus alvei, Rhodotorula glutinis* var. *dairenensis, Pseudomonas stutzeri, Pseudomonas mendocina, Streptomyces coelescens* and *Streptomyces hydrogenans*.

When obtaining 3-hydroxypentanenitrile whose absolute configuration is R-configuration, specific examples of the microorganism are *Arthroascus javanensis* IFO1848, *Candida cantarellii* IFO1261, *Candida fennica* CBS6087, *Candida glabrata* IFO0005, *Candida gropengiesseri* IFO0659, *Candida kefyr* IAM4880, *Candida maris* IFO10003, *Candida melinii* IFO0747, *Candida musae* IFO1582, *Candida pararugosa* IFO0966, *Candida pinus* IFO0741, *Candida sorbophila* IFO1583, *Candida tenuis* IFO0716, *Candida utilis* IFO0639, *Cryptococcus curvatus* IFO1159, *Cryptococcus humicolus* CBS2822, *Debaryomyces hansenii* IFO0063, *Debaryomyces hansenii* var. *fabryi* IFO0015, *Debaryomyces hansenii* var. *hansenii* IFO0032, *Debaryomyces marama* IFO0668, *Debaryomyces nepalensis* IFO0039, *Dekkera anomala* IFO0627, *Geotrichum candidum* CBS187.67, *Geotrichum eriense* ATCC22311, *Geotrichum fermentans* CBS452.83, *Guilliermondella selenospora* IFO 1850, *Issatchenkia orientalis* IFO 1279, *Issatchenkia terricola* IFO0933, *Kluyveromyces marxianus* IFO0288, *Komagataell pastoris* IFO0948, *Komagataella pastoris* IFO1013, *Lipomyces starkeyi* IFO0678, *Lodderomyces elongisporus* IFO1676, *Metschnikowia bicuspidata* IFO1408, *Metschnikowia gruessii* IFO0749, *Ogataea pini* IFO1342, *Ogataea wickerhamii* IFO1706, *Pichia anomala* IFO0120, *Pichia anomala* IFO0144, *Pichia anomala* IFO0146, *Pichia canadensis* IFO0976, *Pichia jadinii* IFO0987, *Pichia petersonii* IFO 1372, *Pichia rhodanensis* IFO1272, *Pichia silvicola* IFO0807, *Pichia triangularis* IFO0836, *Rhodotorula lactosa* IFO1423, *Rhodotorula rubra* IFO0383, *Rhodsporidium diobovatum* IFO0688, *Rhodsporidium sphaerocarpum* IFO1438, *Rhodsporidium toruloides* IFO0413, *Schwanniomyces occidentalis* var. *occidentalis* IFO1840, *Stephanoascus ciferrii* IFO1854, *Torulaspora delbrueckii* IFO0381, *Trichosporon cutaneum* ATCC4151, *Williopsis saturnus* var. *mrakii* IFO0895, *Williopsis saturnus* var. *saturnus* IFO0992, *Williopsis saturnus* var. *suaveolens* IFO0809, *Yarrowia lipolytica* IFO1741, *Acidephilium cyptum* IFO14242, *Agrobacterium tumefacience* IFO12667, *Agrobacterium tumefacience* IFO13265, *Alcaligenes* sp. IFO 14130, *Achromobacter xylosoxidans* subsp. *denitrificans* ATCC15173, *Achromobacter xylosoxidans* subsp. *denitrificans* IFO12669, *Arthrobacter protophormiae* IFO12128, *Cellulomonas gelida* IFO3748, *Comamonas testosteroni* IFO12048, *Microbacterium arborescens* IFO3750, *Rhodococcus equi* JCM1313, *Rhodococcus erythropolis* IAM1452, *Rhodococcus erythropolis* IFO12538, *Rhodococcus erythropolis* IFO 12539, *Rhodococcus rhodochrous* IFO3338, *Candida magnoliae* IFO0705, *Citeromyces matritensis* IFO0651, *Pichia bispora* IFO0803, *Trichosporon loubieri* var. *loubieri* CBS7065, *Corynebacterium ammoniagenes* IFO 12072, *Corynebacterium flavescens* IFO14136, *Devosia riboflavina* IFO13584, *Hofnia alvei* IFO3731, *Proteus vulgaris* IFO3167, *Providencia alcalifaciens* IFO12931, *Absidia coerulea* IFO4011, *Absidia hyalospora* IFO8082, *Aegerita candida* IFO6988, *Agrocybe cylyndracea* IFO30299, *Amylostereum areolatum* IFO9221, *Aspergillus niger* IFO4091, *Aspergillus phoenicis* IFO6670, *Aspergillus sojae* IFO4244, *Corynascucs sepedonium* IFO30067, *Dendryphiella salina* IFO8281, *Emericella nidulans* var. *nidulans* IFO4340, *Emericella unguis* IFO8087, *Fusarium oxysporum* IFO5942, *Fusarium anguioides* IFO4467, *Gibberella fujikuroi* IFO6603, *Glomerella cingulata* IFO5257, *Macrophoma commelinae* IFO9569, *Micronectriella cucumeris* IFO30005, *Mortierella isabellina* IFO7829, *Mortierella ramanniana* var. *angulispora* IFO6744, *Mucor tuberculisporus* IFO9256, *Mucor inaequisporus* IFO8624, *Nannizzia gypsea* var. *incurvata* IFO8306, *Penicillium chermesium* IFO5800, *Penicillium expansum* IFO5854, *Phialophora fastigiata* IFO6850, *Rhizopus niveus* IFO4759, *Rhizopus oryzae* IFO4705, *Sclerotinia sclerotiorum* IFO4876, *Sclerotium delphinii* IFO7337, *Streptomyces cacaoi* subsp. *asoensis* IFO13813 and *Streptomyces* sp. IFO13020. When obtaining 3-hydroxypentanenitrile whose absolute configuration is S-configuration, examples of the microorganism are *Candida albicans* IFO0759, *Candida haemulonii* IFO10001, *Candida intermedia* IFO0761, *Candida maltosa* IFO1977, *Candida mogii* IFO0436, *Candida oleophila* CBS2219, *Dipodascus ovetensis* IFO1201, *Dipodascus tetrasperma* CBS765.70, *Geotrichum fragrans* CBS 164.32, *Hypopichia burtonii* IFO0844, *Kluyveromyces polysporus* IFO0996, *Pichia stipitis* CBS6054, *Schizoblastosporion kobayasii* IFO1644, *Schwanniomyces occidentalis* var. *occidentalis* IFO0371, *Brevundimonas diminuta* IFO12697, *Paenibacillus alvei* IFO3343, *Rhodotorula glutinis* var. *dairenensis* IFO0415, *Pseudomonas stutzeri* IFO13596, *Pseudomonas mendocina* IFO14162, *Streptomyces coelescens* IFO13378 and *Streptomyces hydrogenans* IFO13475.

These microorganisms can usually be obtained from easily obtainable stock strain and can also be isolated from nature. These microorganisms can also be mutated to obtain a strain having properties which are advantageous to the present reaction. Examples of properties which are advantageous to the present invention are improvement of specific activity to 3-ketopentanenitrile and improvement of stereoselectivity. Also, a gene which encodes an enzyme that asymmetrically reduces 3-ketopentanenitrile to optically active 3-hydroxypentanenitrile can be isolated from these microorganisms by a genetic engineering procedure and introduced into any microorganism.

For culturing these microorganisms, usually any medium containing a nutrition source that these microorganisms can assimilate can be used. For example, a common medium, in which a nutrition source, for example, carbon source such as saccharides including glucose, sucrose and maltose, organic acids including lactic acid, acetic acid, citric acid and propionic acid, alcohols including ethanol and glycerin, hydrocarbons including paraffin, fats including soya bean oil and rapeseed oil and mixtures thereof; nitrogen source such as ammonium sulfate, ammonium phosphate, urea, yeast extract, meat extract, peptone and corn-steep liquor; other inorganic salts and vitamins are mixed and compounded accordingly, can be used. The medium can be selected according to the type of microorganism which is used.

The microorganisms can generally be cultured under the usual conditions. For example, culturing aerobically in pH of 4.0 to 9.5 and a temperature range of 20 to 45° C. for 10 to 96 hours is preferable. When the pH is less than 4.0 or more than 9.5 or the temperature is less than 20° C. or more than 45° C., depending on the microorganism to be cultured, the microorganism may not proliferate or the proliferation rate may be extremely slow. When reacting a microorganism with 3-ketopentanenitrile, usually the culture solution itself containing cells of the microorganism can be used for the reaction and concentrate of the culture solution can also be used. Examples of the concentration method are the method of collecting the cells from the culture solution by centrifugation or filtration and then suspending in a small amount of culture supernatant, water or buffer solution and the method of using a centrifugal concentrator. In the case that components in the culture solution affect the reaction, the cells obtained by centrifuging the culture solution or a treated substance thereof can be used.

The treated substance of the microorganism is not particularly limited and examples are dry cells obtained by dehydration with acetone or diphosphorus pentaoxide or by drying using a desiccator or fan, surfactant-treated substances, lytic enzyme-treated substances, immobilized cells or cell-free extract samples in which the cells are fractured. Furthermore, an enzyme that catalyzes the asymmetric reduction reaction can be purified from the culture and used.

In the reduction reaction, 3-ketopentanenitrile which is the substrate can be added all at once in the beginning of the reaction or divided into portions along with the progression of the reaction. As the substrate of the reaction, alkali metal salt of 3-ketopentanenitrile described below can be used as well. The temperature when reacting is preferably 10 to 60° C., more preferably 20 to 40° C. and the pH when reacting is preferably 2.5 to 9, more preferably 5 to 9. When the temperature is less than 10° C. or more than 60° C. or the pH is less than 2.5 or more than 9, depending on the enzyme source which is used, the reaction may not progress or the reaction rate may become extremely slow.

The amount of the enzyme in the reaction solution can be determined according to the ability of the enzyme to reduce the substrate. The concentration of the substrate in the reaction solution is preferably 0.01 to 50% (W/V), more preferably 0.1 to 30% (W/V). When the concentration of the substrate is less than 0.01% (W/V), the amount of 3-hydroxy-pentanetnitrile produced based on the reaction solution is small and efficiency is poor. When the concentration of the substrate is more than 50% (W/V), there is a high possibility that unreacted substrates remain and productivity tends to become poor. The reaction is usually conducted by shaking or aeration agitation. The reaction time is determined according to the concentration of the substrate, the amount of the enzyme and other reaction conditions. Usually, each condition is preferably adjusted so that the reaction finishes in 2 to 168 hours.

In order to advance the reduction reaction, adding an energy source such as glucose, ethanol or isopropanol in a ratio of 0.5 to 30% in the reaction solution is preferable, as excellent effects can be obtained. The reaction can also be advanced by adding a coenzyme such as reduced nicotinamide adenine dinucleotide (hereinafter referred to as NADH) and reduced nicotinamide adenine dinucleotide phosphate (hereinafter referred to as NADPH), which are usually considered to be necessary in a reduction reaction by a biological method. Specifically, in such a case, the coenzymes are added directly to the reaction solution.

Also, in order to advance the reduction reaction, reacting an enzyme, which reduces $NAD^+$ or $NADP^+$ to a reduced form, with a substrate for reducing by coexisting is preferable, as excellent results can be obtained. For example, glucose dehydrogenase as the enzyme that reduces to a reduced form and glucose as the substrate for reducing can coexist or formate dehydrogenase as the enzyme that reduces to a reduced form and formic acid as the substrate for reducing can coexist.

The amount of glucose used is to be at least equimolar to 3-ketopentanenitrile and the amount of glucose dehydrogenase is determined according to the relationship with activity of the reducing enzyme. In the same way, the amount of the formic acid is to be at least equimolar to 3-ketopentanenitrile and the amount of formate dehydrogenase is determined according to the relationship with activity of the reducing enzyme.

Also, adding a surfactant such as Triton (available from Nacalai Tesque, Inc.), Span (available from Kanto Kagaku) and Tween (available from Nacalai Tesque, Inc.) to the reaction solution is effective. Furthermore, in order to avoid inhibition of the reaction due to the substrate and/or alcohol body which is a product of the reduction reaction, a water-insoluble organic solvent such as ethyl acetate, butyl acetate, isopropyl ether, toluene and hexane can be added. In order to improve the solubility of the substrate, a water-soluble organic solvent such as methanol, ethanol, acetone, tetrahydrofurane and dimethylsulfoxide can be added.

The method for collecting optically active 3-hydroxypentanenitrile produced from the reduction reaction is not particularly limited. However, high-purity optically active 3-hydroxypentanenitrile can easily be obtained by directly extracting the reaction solution or extracting the substance obtained by separating cells from the reaction solution with a solvent such as ethyl acetate, toluene, t-butyl methyl ether or hexane, dehydrating and purifying by distillation or silica gel column chromatography.

After the conversion reaction, extraction is conducted with a suitable organic solvent and by analyzing the produced 3-hydroxypentanenitrile with capillary gas chromatography, the molar yield, absolute configuration and optical purity of the produced 3-hydroxypentanenitrile can be found.

Below, alkali metal salt of 3-ketopentanenitrile is described.

In the presence of an alkali metal base, 3-ketopentanenitrile is synthesized from propionic acid ester and acetonitrile. Preferable examples of the alkali metal base used are alkali metal base such as sodium ethoxide, sodium methoxide, sodium hydride, potassium ethoxide, potassium methoxide, potassium hydride and lithium hydride. Of these, in view of yield, sodium hydride is more preferable. Examples of the propionic acid ester are methyl propionate, ethyl propionate and butyl propionate. Preferable examples of the catalyst when reacting are tetrahydrofurane, ether, benzene, ethanol and methanol are preferable. Of these, in view of yield, tetrahydrofurane is more preferable. The reaction temperature can be adjusted depending on the progression of the reaction and is preferably adjusted under reflux conditions.

The reaction is conducted under the above conditions and when production of 3-ketopentanenitrile is confirmed, alkali metal salt of 3-ketopentanenitrile can be precipitated as white crystal by cooling the reaction solution. Also, alkali metal salt of 3-ketopentanenitrile can be precipitated by adding a solvent that prevents alkali metal salt of 3-ketopentanenitrile from dissolving into the reaction solution. Examples of the solvent that prevents alkali metal salt of 3-ketopentanenitrile from dissolving are n-hexane, heptane and petroleum ether. The alkali metal salt of 3-ketopentanenitrile precipitated in the reaction solution can be isolated by filtering the reaction solution. The type of alkali metal of the obtained alkali metal salt of 3-ketopentanenitrile is the same as the type of alkali metal used in the synthesis reaction.

As described above, in addition to 3-ketopentanenitrile, the obtained alkali metal salt of 3-ketopentanenitrile can be used as a raw material when synthesizing optically active 3-hydroxypentanenitrile by action of an enzyme.

Hereinafter, the present invention is described in detail based on Examples but the present invention is not limited thereto. In the following descriptions, "%" represents "% by weight" unless specified otherwise.

EXAMPLE 1

A large scale test tube was charged with 5 ml of a liquid medium (pH 7) comprising 40 g of glucose, 3 g of yeast extract, 6.5 g of diammonium hydrogenphosphate, 1 g of potassium dihydrogenphosphate, 0.8 g of magnesium sulfate heptahydrate, 60 mg of zinc sulfate heptahydrate, 90 mg of iron sulfate heptahydrate, 5 mg of copper sulfate pentahydrate, 10 mg of manganese sulfate tetrahydrate and 100 mg of sodium chloride (all per 1 L) and sterilized by steam at 120° C. for 20 minutes. One loop of the microorganisms shown in Table 1 were aseptically inoculated into the liquid solution and cultured by shaking at 30° C. for 72 hours. After culturing, 2.5 ml of each culture solution was centrifuged to collect the cells of the microorganism and each of the cells were suspended in 0.5 ml of a 100 mM phosphate buffer solution (pH 6.5) containing 4% of glucose. The cell suspension was added into a test tube in which 5 mg of 3-ketopentanenitrile was added in advance and reacted for 24 hours at 30° C. After the reaction, 1 ml of ethyl acetate was added to each reaction solution and mixed thoroughly and part of the organic layer was analyzed under the following capillary gas chromatography analysis conditions.

[Capillary Gas Chromatography Analysis Conditions]
column: Chiraldex G-TA made by ASTEC, Inc. (20 m×0.25 mm)
detection: FID
column temperature: 130° C.
injection temperature: 200° C.
detection temperature: 200° C.
carrier gas: helium (100 kPa)
split ratio: 100/1
elution time: (R)-3-hydroxypentanenitrile 3.23 minutes, (S)-3-hydroxypentanenitrile 3.67 minutes The molar yield, optical purity and absolute configuration of the produced 3-hydroxypentanenitrile are shown in Table 1.

EXAMPLE 2

The microorganisms shown in Table 2 were cultured and collected in the same manner as in Example 1. Cells of each microorganism were suspended in 0.5 ml of a 100 mM phosphate buffer solution (pH 6.5) containing 0.739 mg of NAD$^+$, 0.862 mg of NADP$^+$, 13.9 mg of glucose, 3 U of glucose dehydrogenase (product name: GLUCDH "Amano" II, available from Amano Enzyme, Inc.). The cell suspension was added into a test tube in which 5 mg of 3-ketopentanenitrile and 0.5 ml of butyl acetate were added in advance and reacted for 24 hours at 30° C. After the reaction, 0.5 ml of ethyl acetate was added to each reaction solution and mixed thoroughly and part of the organic layer was analyzed by the same analysis method as in Example 1. The molar yield, optical purity and absolute configuration of the produced 3-hydroxypentanenitrile are shown in Table 2.

TABLE 1

| Microorganism | | | Molar yield (%) | Optical Purity (% e.e.) | Absolute Configuration |
|---|---|---|---|---|---|
| Arthroascus | javanensis | IFO 1848 | 5.9 | 85.1 | R |
| Candida | cantarellii | IFO 1261 | 60.2 | 73.6 | R |
| Candida | magnoliae | IFO 0705 | 30.0 | 77.0 | R |
| Candida | glabrata | IFO 0005 | 5.3 | 82.4 | R |
| Candida | gropengiesseri | IFO 0659 | 56.9 | 81.7 | R |
| Candida | pararugosa | IFO 0966 | 39.1 | 83.1 | R |
| Candida | pinus | IFO 0741 | 14.9 | 80.7 | R |
| Candida | sorbophila | IFO 1583 | 41.0 | 74.7 | R |
| Candida | fennica | CBS 6087 | 67.0 | 76.2 | R |
| Candida | tenuis | IFO 0716 | 9.0 | 75.0 | R |
| Citeromyces | matritensis | IFO 0651 | 7.7 | 89.5 | R |
| Cryptococcus | curvatus | IFO 1159 | 52.1 | 75.5 | R |
| Cryptococcus | humicolus | CBS 2822 | 61.2 | 75.2 | R |
| Debaryomyces | hansenii var. fabryi | IFO 0015 | 67.8 | 87.1 | R |
| Debaryomyces | marama | IFO 0668 | 36.7 | 79.8 | R |
| Debaryomyces | nepalensis | IFO 0039 | 44.1 | 94.8 | R |
| Geotrichum | candidum | CBS 187.67 | 55.0 | 76.7 | R |
| Geotrichum | eriense | ATCC 22311 | 60.1 | 74.6 | R |
| Geotrichum | fermentans | CBS 452.83 | 58.2 | 78.7 | R |
| Guilliermondella | selenospora | IFO 1850 | 63.7 | 77.3 | R |
| Issatchenkia | terricola | IFO 0933 | 13.0 | 87.3 | R |
| Komagataella | pastoris | IFO 0948 | 6.9 | 83.1 | R |
| Komagataella | pastoris | IFO 1013 | 5.7 | 85.5 | R |
| Lipomyces | starkeyi | IFO 0678 | 26.3 | 79.2 | R |
| Ogataea | pini | IFO 1342 | 5.0 | 86.1 | R |
| Pichia | anomala | IFO 0146 | 12.5 | 85.6 | R |
| Pichia | silvicola | IFO 0807 | 68.0 | 75.7 | R |
| Rhodsporidium | sphaerocarpum | IFO 1438 | 51.2 | 74.2 | R |
| Rhodsporidium | toruloides | IFO 0413 | 72.1 | 76.9 | R |
| Rhodotorula | rubra | IFO 0383 | 6.2 | 70.7 | R |
| Trichosporon | cutaneum | ATCC 4151 | 18.4 | 94.0 | R |
| Yarrowia | lipolytica | IFO 1741 | 6.2 | 82.3 | R |

TABLE 2

| Microorganism | | | Molar yield (%) | Optical Purity (% e.e.) | Absolute Configuration |
|---|---|---|---|---|---|
| Candida | glabrata | IFO 0005 | 6.9 | 76.4 | R |
| Candida | gropengiesseri | IFO 0659 | 11.3 | 83.0 | R |
| Candida | kefyr | IAM 4880 | 19.1 | 76.9 | R |
| Candida | pinus | IFO 0741 | 8.1 | 79.6 | R |
| Candida | utilis | IFO 0639 | 18.2 | 81.0 | R |
| Cryptococcus | humicola | CBS 2822 | 5.2 | 83.5 | R |
| Debaryomyces | hansenii | IFO 0063 | 11.1 | 83.8 | R |
| Debaryomyces | hansenii var. hansenii | IFO 0032 | 9.8 | 83.2 | R |
| Debaryomyces | hansenii var. fabryi | IFO 0015 | 9.6 | 85.8 | R |
| Dekkera | anomala | IFO 0627 | 9.7 | 86.0 | R |
| Kluyveromyces | marxianus | IFO 0288 | 15.3 | 90.8 | R |
| Komagataella | pastoris | IFO 0948 | 50.2 | 83.3 | R |
| Metschnikowia | bicuspidata | IFO 1408 | 15.3 | 80.8 | R |
| Metschnikowia | gruessii | IFO 0749 | 11.1 | 78.6 | R |
| Pichia | anomala | IFO 0120 | 18.7 | 87.8 | R |
| Pichia | anomala | IFO 0144 | 10.2 | 80.8 | R |
| Pichia | bispora | IFO 0803 | 4.3 | 92.9 | R |
| Pichia | jadinii | IFO 0987 | 29.9 | 78.1 | R |
| Pichia | petersonii | IFO 1372 | 9.9 | 75.8 | R |
| Pichia | silvicola | IFO 0807 | 24.1 | 76.2 | R |
| Rhodotorula | lactosa | IFO 1423 | 6.5 | 76.3 | R |
| Schwanniomyces | occidentalis var. occidentalis | IFO 1840 | 10.6 | 79.3 | R |
| Stephanoascus | ciferrii | IFO 1854 | 8.7 | 76.7 | R |
| Torulaspora | delbrueckii | IFO 0381 | 10.9 | 86.2 | R |
| Trichosporon | loubieri var. loubieri | CBS 7065 | 7.7 | 85.1 | R |
| Williopsis | saturnus var. suaveolens | IFO 0809 | 17.0 | 87.3 | R |
| Williopsis | saturnus var. saturnus | IFO 0992 | 16.3 | 87.6 | R |
| Yarrowia | lipolytica | IFO 1741 | 6.2 | 79.8 | R |
| Candida | haemulonii | IFO 10001 | 18.3 | 82.8 | S |
| Candida | albicans | IFO 0759 | 7.2 | 88.2 | S |
| Dipodascus | ovetensis | IFO 1201 | 27.7 | 62.4 | S |
| Dipodascus | tatrasperma | CBS 765.70 | 54.6 | 81.1 | S |
| Geotrichum | fragrans | CBS 164.32 | 32.9 | 86.5 | S |
| Hyphopichia | burtonii | IFO 0844 | 13.8 | 80.9 | S |
| Kluyveromyces | polysporus | IFO 0996 | 3.3 | 74.7 | S |
| Pichia | stipitis | CBS 6054 | 31.3 | 64.5 | S |
| Rhodotorula | glutinis var. dairenensis | IFO 0415 | 5.7 | 75.7 | S |
| Schwanniomyces | occidentalis var. occidentalis | IFO 0371 | 32.2 | 85.3 | S |

EXAMPLE 3

A 500 ml Sakaguchi flask was charged with 45 ml of a liquid medium comprising 40 g of glucose, 3 g of yeast extract, 6.5 g of diammonium hydrogenphosphate, 1 g of potassium dihydrogenphosphate, 0.8 g of magnesium sulfate heptahydrate, 60 mg of zinc sulfate heptahydrate, 90 mg of iron sulfate heptahydrate, 5 mg of copper sulfate pentahydrate, 10 mg of manganese sulfate tetrahydrate and 100 mg of sodium chloride (all per 900 ml) and 1 drop of adecanol and then sterilized. 5 ml of a sterilized 40% glucose aqueous solution was added thereto and one loop of the microorganisms shown in Table 3 were aseptically inoculated and cultured by shaking at 30° C. for 72 hours. After culturing, cells of the microorganisms were collected by centrifugation and washed twice with deionized water. The wet cells were suspended in 40 ml of deionized water. 1.2 L of acetone was added while stirring and cooling with ice and agitation was conducted for 30 minutes in ice. The solution was filtered and the cells on the filter paper were washed with cooled acetone. Drying was conducted under reduced pressure and the acetone-dried cells of the microorganisms shown in Table 3 were respectively obtained.

With respect to each of the acetone-dried cells obtained by the above method, 10 mg of the acetone-dried cells, 0.739 mg of $NAD^+$, 13.9 mg of glucose, 3 U of glucose dehydrogenase (product name: GLUCDH "Amano" II, available from Amano Enzyme, Inc.), 0.5 ml of a 100 mM phosphate buffer solution (pH 6.5) and 5 mg of 3-ketopentanenitrile were added into a test tube and reacted for 24 hours at 30° C. After the reaction, 1 ml of ethyl acetate was added to each reaction solution and mixed thoroughly and part of the organic layer was analyzed by the same analysis method as in Example 1. The molar yield, optical purity and absolute configuration of the produced 3-hydroxypentanenitrile are shown in Table 3.

TABLE 3

| Microorganism | | | Molar yield (%) | Optical Purity (% e.e.) | Absolute Configuration |
|---|---|---|---|---|---|
| Candida | maris | IFO 10003 | 22.0 | 79.0 | R |
| Candida | melinii | IFO 0747 | 18.0 | 94.5 | R |
| Issatchenkia | orientalis | IFO 1279 | 25.2 | 54.9 | R |
| Issatchenkia | terricola | IFO 0933 | 8.2 | 73.7 | R |
| Ogataea | pini | IFO 1342 | 3.8 | 73.4 | R |

TABLE 3-continued

| Microorganism | | | Molar yield (%) | Optical Purity (% e.e.) | Absolute Configuration |
|---|---|---|---|---|---|
| Ogataea | wickerhamii | IFO 1706 | 13.9 | 71.7 | R |
| Pichia | anomala | IFO 0120 | 31.1 | 88.7 | R |
| Pichia | anomala | IFO 0144 | 14.0 | 79.0 | R |
| Pichia | canadensis | IFO 0976 | 32.3 | 75.6 | R |
| Williopsis | saturnus var. mrakii | IFO 0895 | 36.7 | 83.0 | R |
| Williopsis | saturnus var. saturnus | IFO 0992 | 20.7 | 88.2 | R |
| Williopsis | saturnus var. suaveolens | IFO 0809 | 54.0 | 83.8 | R |
| Yarrowia | lipolytica | IFO 1741 | 12.8 | 78.7 | R |
| Candida | Intermedia | IFO 0761 | 23.2 | 75.7 | S |
| Candida | maltosa | IFO 1977 | 31.8 | 91.5 | S |
| Candida | mogii | IFO 0436 | 43.8 | 90.8 | S |
| Candida | oleophila | CBS 2219 | 49.0 | 89.2 | S |
| Candida | albicans | IFO 0759 | 23.5 | 93.5 | S |
| Schizoblastosporion | kobayasii | IFO 1644 | 37.2 | 87.7 | S |

EXAMPLE 4

Acetone-dried cells of the microorganisms shown in Table 4 were respectively obtained in the same manner as in Example 3. With respect to each of the acetone-dried cells, 10 mg of the acetone-dried cells, 0.862 mg of NADP+,13.9 mg of glucose, 3 U of glucose dehydrogenase (product name: GLUCDH "Amano" II, available from Amano Enzyme, Inc.), 0.5 ml of a 100 mM phosphate buffer solution (pH 6.5) and 5 mg of 3-ketopentanenitrile were added into a test tube and reacted for 24 hours at 30° C. After the reaction, 1 ml of ethyl acetate was added to each reaction solution and mixed thoroughly and part of the organic layer was analyzed by the same analysis method as in Example 1. The molar yield, optical purity and absolute configuration of the produced 3-hydroxypentanenitrile are shown in Table 4.

EXAMPLE 5

A large scale test tube was charged with 7 ml of a liquid medium (pH 7) comprising 10 g of meat extract, 10 g of peptone, 5 g of yeast extract and 3 g of sodium chloride (all per 1 L) and sterilized by steam at 120° C. for 20 minutes. One loop of the microorganisms shown in Table 5 were aseptically inoculated into the liquid solution and cultured by shaking at 30° C. for 36 hours. After culturing, 3.5 ml of each culture solution was centrifuged to collect cells of the microorganisms and each of the cells were suspended in 0.5 ml of a 100 mM phosphate buffer solution (pH 6.5) containing 8% of glucose. The cell suspension was added into a test tube in which 5 mg of 3-ketopentanenitrile was added in advance and reacted for 18 hours at 30° C. After the reaction, analysis was conducted in the same manner as in

TABLE 4

| Microorganism | | | Molar yield (%) | Optical Purity (% e.e.) | Absolute Configuration |
|---|---|---|---|---|---|
| Candida | glabrata | IFO 0005 | 13.3 | 78.8 | R |
| Candida | gropengiesseri | IFO 0659 | 30.1 | 79.7 | R |
| Candida | melinii | IFO 0747 | 14.4 | 89.9 | R |
| Candida | musae | IFO 1582 | 20.4 | 84.0 | R |
| Candida | sorbophila | IFO 1583 | 21.8 | 79.5 | R |
| Candida | tenuis | IFO 0716 | 11.1 | 81.4 | R |
| Cryptococcus | humicola | CBS 2822 | 16.4 | 82.5 | R |
| Debaryomyces | hansenii | IFO 0063 | 15.2 | 84.7 | R |
| Debaryomyces | hansenii var. hansenii | IFO 0032 | 16.0 | 82.3 | R |
| Debaryomyces | hansenii var. fabryi | IFO 0015 | 17.5 | 86.2 | R |
| Dekkera | anomala | IFO 0627 | 14.3 | 80.5 | R |
| Issatchenkia | orientalis | IFO 1279 | 17.4 | 50.8 | R |
| Issatchenkia | terricola | IFO 0933 | 6.9 | 70.3 | R |
| Lodderomyces | elongisporus | IFO 1676 | 12.5 | 77.4 | R |
| Metschnikowia | bicuspidata | IFO 1408 | 15.3 | 79.3 | R |
| Ogataea | pini | IFO 1342 | 4.5 | 76.8 | R |
| Ogataea | wickerhamii | IFO 1706 | 6.8 | 59.7 | R |
| Pichia | anomala | IFO 0120 | 32.2 | 88.2 | R |
| Pichia | anomala | IFO 0144 | 10.3 | 76.5 | R |
| Pichia | rhodanensis | IFO 1272 | 46.5 | 85.0 | R |
| Pichia | triangularis | IFO 0836 | 11.8 | 79.9 | R |
| Rhodsporidium | diobovatum | IFO 0688 | 21.4 | 81.1 | R |
| Rhodsporidium | sphaerocarpum | IFO 1438 | 13.7 | 78.8 | R |
| Rhodotorula | rubra | IFO 0383 | 28.0 | 76.3 | R |
| Williopsis | saturnus var. saturnus | IFO 0992 | 14.8 | 87.1 | R |
| Yarrowia | lipolytica | IFO 1741 | 36.9 | 81.4 | R |
| Candida | mogii | IFO 0436 | 41.7 | 69.3 | S |
| Dipodascus | tetrasperma | CBS 765.70 | 18.9 | 71.8 | S |

Example 1. The molar yield, optical purity and absolute configuration of the produced 3-hydroxypentanenitrile are shown in Table 5.

TABLE 5

| Microorganism | | | Molar yield (%) | Optical purity (% e.e.) | Absolute Configuration |
|---|---|---|---|---|---|
| *Achromobacter* | *xylosoxidans* subsp. *denitrificans* | IFO 12669 | 8.9 | 77.4 | R |
| *Achromobacter* | *xylosoxidans* subsp. *denitrificans* | ATCC 15173 | 18.3 | 78.3 | R |
| *Arthrobacter* | *protophormiae* | IFO 12128 | 12.8 | 77.3 | R |
| *Acidiphilium* | *cryptum* | IFO 14242 | 6.2 | 91.3 | R |
| *Cellulomonas* | *gelida* | IFO 3748 | 7.1 | 84.1 | R |
| *Corynebacterium* | *ammoniagenes* | IFO 12072 | 7.7 | 79.9 | R |
| *Corynebacterium* | *flavescens* | IFO 14136 | 5.7 | 78.4 | R |
| *Devosia* | *riboflavina* | IFO 13584 | 7.0 | 85.7 | R |
| *Microbacterium* | *arborescens* | IFO 3750 | 6.3 | 71.0 | R |
| *Rhodococcus* | *erythropolis* | IFO 12538 | 9.6 | 79.6 | R |
| *Rhodococcus* | *erythropolis* | IFO 12539 | 5.0 | 70.3 | R |
| *Rhodococcus* | *erythropolis* | IAM 1452 | 15.0 | 80.0 | R |
| *Rhodococcus* | *rhodochrous* | IFO 3338 | 5.5 | 87.9 | R |

EXAMPLE 6

The microorganisms shown in Table 6 were cultured and collected in the same manner as in Example 5. Cells of each microorganism were suspended in 0.5 ml of a 100 mM phosphate buffer solution (pH 6.5) containing 0.739 mg of $NAD^+$, 0.862 mg of $NADP^+$, 13.9 mg of glucose and 3 U of glucose dehydrogenase (product name: GLUCDH "Amano" II, available from Amano Enzyme, Inc.). The cell suspension was added into a test tube in which 5 mg of 3-ketopentanenitrile and 0.5 ml of butyl acetate were added in advance and reacted for 24 hours at 30° C. After the reaction, 0.5 ml of ethyl acetate was added to each reaction solution and mixed thoroughly and part of the organic layer was analyzed by the same analysis method as in Example 1. The molar yield, optical purity and absolute configuration of the produced 3-hydroxypentanenitrile are shown in Table 6.

TABLE 6

| Microorganism | | | Molar yield (%) | Optical Purity (% e.e.) | Absolute Configuration |
|---|---|---|---|---|---|
| *Alcaligenes* | sp. | IFO 14130 | 3.5 | 78.0 | R |
| *Agrobacterium* | *tumefaciens* | IFO 12667 | 3.6 | 73.4 | R |
| *Agrobacterium* | *tumefaciens* | IFO 13265 | 3.1 | 71.2 | R |
| *Comamonas* | *testosteroni* | IFO 12048 | 14.3 | 78.5 | R |
| *Hofnia* | *alvei* | IFO 3731 | 5.0 | 86.6 | R |
| *Proteus* | *vulgaris* | IFO 3167 | 3.5 | 79.9 | R |
| *Providencia* | *alcalifaciens* | IFO 12931 | 3.5 | 83.1 | R |
| *Rhodococcus* | *equi* | JCM 1313 | 4.1 | 76.3 | R |
| *Brevundimonas* | *diminuta* | IFO 12697 | 70.0 | 63.5 | S |
| *Paenibacillus* | *alvei* | IFO 3343 | 5.7 | 76.4 | S |
| *Pseudomonas* | *stutzeri* | IFO 13596 | 24 | 50.5 | S |
| *Pseudomonas* | *mendocina* | IFO 14162 | 3.7 | 45.9 | S |

EXAMPLE 7

22 g of 60% sodium hydride was suspended in 400 ml of tetrahydrofurane. Then, while heating, 24.7 g of acetonitrile and subsequently 58.3 g of ethyl propionate were dropped and agitated overnight at 80° C. After naturally cooling to room temperature, the mixture was cooled further in ice water. The precipitated white crystal was obtained by filtration and dried under reduced pressure after washing with 350 ml of n-hexane. 45.0 g of white crystal 3-ketopentanenitrile-sodium salt was obtained.

EXAMPLE 8

40 g of 60% sodium hydride was suspended in 300 ml of tetrahydrofurane. Then, while heating, 49.3 g of acetonitrile and subsequently 122.56 g of ethyl propionate were dropped and agitated overnight at 80° C. After naturally cooling to room temperature, 300 ml of n-hexane was added while cooling further in ice water. The precipitated white crystal was obtained by filtration and dried under reduced pressure after washing with 500 ml of n-hexane. 98.7 g of white crystal 3-ketopentanenitrile-sodium salt was obtained.

EXAMPLE 9

*Candida gropengiesseri* IFO0659 was cultured in the same manner as in Example 3 and 1 L of the obtained culture solution was centrifuged to collect cells of the microorganism. The cells were suspended in 200 ml of a 100 mM phosphate buffer solution (pH 6.5) containing 4% of glucose. To this cell suspension, 1.19 g of 3-ketopentanenitrile-sodium salt was added while maintaining pH 6.5 using 6N hydrochloric acid. After adding, the reaction was conducted by agitating for 24 hours at 30° C. After the reaction, the aqueous phase was extracted with ethyl acetate and then extracted further with ethyl acetate. The organic phase was then combined and dehydration was conducted with anhydrous sodium sulfate. Thereafter, the solvent was removed under reduced pressure and purification was conducted by silica gel chromatography. 842 mg of 3-hydroxypentanenitrile was obtained. The optical purity found from the method described in Example 1 was 81.7% e.e. in R-configuration.
$^1$H-NMR $\delta(CDCl_3)$:1.00 (3H, t), 1.64 (2H, dq), 2.27 (1H, s), 2.54 (2H, dd), 3.86–3.92 (1H, m).

EXAMPLE 10

The reaction and analysis were conducted in the same manner as in Example 1 except that the microorganisms shown in Table 7 were cultured in a medium (pH 6.0) comprising 5% of glucose and 5% of corn-steep liquor. The molar yield, optical purity and absolute configuration of the produced 3-hydroxypentanenitrile are shown in Table 7.

TABLE 7

| Microorganism | | | Molar yield (%) | Optical purity (% e.e.) | Absolute configuration |
|---|---|---|---|---|---|
| Absidia | coerulea | IFO 4011 | 17.4 | 84.6 | R |
| Absidia | hyalospora | IFO 8082 | 10.8 | 87.9 | R |
| Aegerita | Candida | IFO 6988 | 6.1 | 86.8 | R |
| Agrocybe | cylyndracea | IFO 30299 | 14.7 | 88.1 | R |
| Amylostereum | areolatum | IFO 9221 | 12.9 | 87.8 | R |
| Aspergillus | niger | IFO 4091 | 5.6 | 87.9 | R |
| Aspergillus | phoenicis | IFO 6670 | 3.7 | 87.3 | R |
| Aspergillus | sojae | IFO 4244 | 6.5 | 86.7 | R |
| Corynascus | sepedonium | IFO 30067 | 17.2 | 80.0 | R |
| Dendryphiella | salina | IFO 8281 | 12.8 | 81.6 | R |
| Emericella | nidulans var. nidulans | IFO 4340 | 6.9 | 88.1 | R |
| Emericella | unguis | IFO 8087 | 73.0 | 85.3 | R |
| Fusarium | oxysporum | IFO 5942 | 35.7 | 88.5 | R |
| Fusarium | anguioides | IFO 4467 | 13.2 | 84.9 | R |
| Gibberella | fujikuroi | IFO 6603 | 16.1 | 85.7 | R |
| Glomerella | cingulata | IFO 5257 | 21.7 | 86.1 | R |
| Macrophoma | commelinae | IFO 9569 | 40.6 | 74.1 | R |
| Micronectriella | cucumeris | IFO 30005 | 26.7 | 80.8 | R |
| Mortierella | isabellina | IFO 7829 | 59.9 | 85.2 | R |
| Mortierella | ramanniana var. angulispora | IFO 6744 | 23.1 | 86.2 | R |
| Mucor | tuberculisporus | IFO 9256 | 61.0 | 82.6 | R |
| Mucor | inaequisporus | IFO 8624 | 56.5 | 84.0 | R |
| Nannizzia | gypsea var. incurvata | IFO 8306 | 20.5 | 87.6 | R |
| Penicillium | chermesium | IFO 5800 | 26.7 | 86.9 | R |
| Penicillium | expansum | IFO 5854 | 14.9 | 85.8 | R |
| Phialophora | fastigiata | IFO 6850 | 8.6 | 87.4 | R |
| Rhizopus | niveus | IFO 4759 | 12.9 | 82.0 | R |
| Rhizopus | oryzae | IFO 4705 | 13.0 | 81.8 | R |
| Sclerotinia | sclerotiorum | IFO 4876 | 6.0 | 87.7 | R |
| Sclerotium | delphinii | IFO 7337 | 13.9 | 87.2 | R |

EXAMPLE 11

The reaction and analysis were conducted in the same manner as in Example 1 except that the microorganisms shown in Table 8 were cultured in a medium (pH 7.2) comprising 3% of Tryptic Soy Broth available from Difco Laboratories and 1% of soluble starch. The molar yield, optical purity and absolute configuration of the produced 3-hydroxypentanenitrile are shown in Table 8.

TABLE 8

| Microorganism | | | Molar yield (%) | Optical purity (% e.e.) | Absolute configuration |
|---|---|---|---|---|---|
| Streptomyces | cacaoi subsp. asoensis | IFO 13813 | 5.3 | 64.5 | R |
| Streptomyces | sp. | IFO 13020 | 3.7 | 53.7 | R |
| Streptomyces | coelescens | IFO 13378 | 12.2 | 39.2 | S |
| Streptomyces | hydrogenans | IFO 13475 | 3.5 | 51.5 | S |

INDUSTRIAL APPLICABILITY

According to the present invention, optically active 3-hydroxypentanenitrile can be prepared with high yield by stereoselectively reducing 3-ketopentanenitrile by action of an enzyme having asymmetric reduction activity. Also, alkali metal salt of 3-ketopentanenitrile, which is a stable compound without problems regarding storage, can be efficiently obtained.

The invention claimed is:

1. A process for preparing optically active 3-hydroxypentanenitrile of the formula (1)

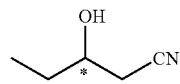

(1)

comprising: asymmetrically enzymatically reducing 3-ketopentanenitrile of formula (2)

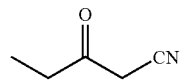

(2)

or an alkali metal salt of 3-ketopentanenitrile of formula (3) wherein M is an alkali metal, in a reaction mixture with an enzyme to produce optically active 3-hydroxypentanenitrile and recovering the product.

2. The process of claim 1, wherein said enzyme is an enzyme present in a cell, a culture solution or a treated substance thereof or a purified enzyme obtained from a microorganism selected from the group consisting of Arthroascus genus, Candida genus, Cryptococcus genus, Debaryomyces genus, Dekkera genus, Dipodascus genus, Geotrichum genus, Guilliermondella genus, Hyphopichia genus, Issatchenkia genus, Kluyveromyces genus, Komagataella genus, Lipomyces genus, Lodderomyces genus, Metschnikowia genus, Ogataea genus, Pichia genus, Rhodotorula genus, Rhodsporidium genus, Schizoblastosporion genus, Schwanniomyces genus, Stephanoascus genus, Torulaspora genus, Trichosporon genus, Williopsis genus, Yarrowia genus, Acidephilium genus, Agrobacterium genus, Alcaligenes genus, Arthrobacter genus, Brevundimonas genus, Cellulomonas genus, Comamonas genus, Microbacterium genus, Paenibacillus genus, Rhodococcus genus, Citeromyces genus, Achromobacter genus, Corynebacterium genus, Devosia genus, Hofnia genus, Proteus genus, Providencia genus, Pseudomonas genus, Absidia genus, Aegerita genus, Agrocybe genus, Amylostereum genus, Aspergillus genus, Corynascucs genus, Dendryphiella genus, Emericella genus, Fusarium genus, Gibberella genus, Glomerella genus, Macrophoma genus, Micronectriella genus, Mortierella genus, Mucor genus, Nannizzia genus, Penicillium genus, Phialophora genus, Rhizopus genus, Sclerotinia genus, Sclerotium genus and Streptomyces genus.

3. The process of claim 1, wherein absolute configuration of said produced optically active 3-hydroxypentanenitrile is R-configuration and said enzyme is an enzyme present in a cell, a culture solution or a treated substance thereof or a purified enzyme obtained from a microorganism selected from the group consisting of *Arthroascus* genus, *Candida* genus, *Cryptococcus* genus, *Debaryomyces* genus, *Dekkera* genus, *Geotrichum* genus, *Guilliermondella* genus, *Issatchenkia* genus, *Kluyveromyces* genus, *Komagataella* genus, *Lipomyces* genus, *Lodderomyces* genus, *Metschnikowia* genus, *Ogataea* genus, *Pichia* genus, *Rhodotorula* genus, *Rhodsporidium* genus, *Schwanniomyces* genus, *Stephanoascus* genus, *Torulaspora* genus, *Trichosporon* genus, *Williopsis* genus, *Yarrowia* genus, *Acidephilium* genus, *Agrobacterium* genus, *Alcaligenes* genus, *Arthrobacter* genus, *Cellulomonas* genus, *Comamonas* genus, *Microbacterium* genus, *Rhodococcus* genus, *Citeromyces* genus, *Achromobacter* genus, *Corynebacterium* genus, *Devosia* genus, *Hofnia* genus, *Proteus* genus, *Providencia* genus, *Absidia* genus, *Aegerita* genus, *Agrocybe* genus, *Amylostereum* genus, *Aspergillus* genus, *Corynascucs* genus, *Dendryphiella* genus, *Emericella* genus, *Fusarium* genus, *Gibberella* genus, *Glomerella* genus, *Macrophoma* genus, *Micronectriella* genus, *Mortierella* genus, *Mucor* genus, *Nannizzia* genus, *Penicillium* genus, *Phialophora* genus, *Rhizopus* genus, *Sclerotinia* genus, *Sclerotium* genus and *Streptomyces* genus.

4. The process of claim 1, wherein absolute configuration of said produced optically active 3-hydroxypentanenitrile is R-configuration and said enzyme is an enzyme present in a cell, a culture solution or a treated substance thereof or a purified enzyme obtained from a microorganism selected from the group consisting of *Arthroascus javanensis*, *Candida cantarellii*, *Candida fennica*, *Candida glabrata*, *Candida gropengiesseri*, *Candida kefyr*, *Candida maris*, *Candida melinii*, *Candida musae*, *Candida pararugosa*, *Candida pinus*, *Candida sorbophila*, *Candida tenuis*, *Candida utilis*, *Cryptococcus curvatus*, *Cryptococcus humicolus*, *Debaryomyces hansenii*, *Debaryomyces hansenii* var. *fabryi*, *Debaryomyces hansenii* var. *hansenii*, *Debaryomyces marama*, *Debaryomyces nepalensis*, *Dekkera anomala*, *Geotrichum candidum*, *Geotrichum eriense*, *Geotrichum fermentans*, *Guilliermondella selenospora*, *Issatchenkia orientalis*, *Issatchenkia terricola*, *Kluyveromyces marxianus*, *Komagataella pastoris*, *Lipomyces starkeyi*, *Lodderomyces elongisporus*, *Metschnikowia bicuspidata*, *Metschnikowia gruessii*, *Ogataea pini*, *Ogataea wickerhamii*, *Pichia anomala*, *Pichia canadensis*, *Pichia jadinii*, *Pichia petersonii*, *Pichia rhodanensis*, *Pichia silvicola*, *Pichia triangularis*, *Rhodotorula lactosa*, *Rhodotorula rubra*, *Rhodsporidium diobovatum*, *Rhodsporidium sphaerocarpum*, *Rhodsporidium toruloides*, *Schwanniomyces occidentalis* var. *occidentalis*, *Stephanoascus ciferrii*, *Torulaspora delbrueckii*, *Trichosporon cutaneum*, *Williopsis saturnus* var. *mrakii*, *Williopsis saturnus* var. *saturnus*, *Williopsis saturnus* var. *suaveolens*, *Yarrowia lipolytica*, *Acidephilium cryptum*, *Agrobacterium tumefaciense*, *Alcaligenes* sp., *Achromobacter xylosoxidans* subsp. *denitrificans*, *Arthrobacter protophormiae*, *Cellulomonas gelida*, *Comamonas testosteroni*, *Microbacterium arborescens*, *Rhodococcus equi*, *Rhodococcus erythropolis*, *Rhodococcus rhodochrous*, *Candida magnoliae*, *Citeromyces matritensis*, *Pichia bispora*, *Trichosporon loubieri* var. *loubieri*, *Corynebacterium ammoniagenes*, *Corynebacterium flavescens*, *Devosia riboflavina*, *Hofnia alvei*, *Proteus vulgaris*, *Providencia alcalifaciens*, *Absidia coerulea*, *Absidia hyalospora*, *Aegerita candida*, *Agrocybe cylyndracea*, *Amylostereum areolatum*, *Aspergillus niger*, *Aspergillus phoenicis*, *Aspergillus sojae*, *Corynascucs sepedonium*, *Dendryphiella salina*, *Emericella nidulans* var. *nidulans*, *Emericella unguis*, *Fusarium oxysporum*, *Fusarium anguioides*, *Gibberella fujikuroi*, *Glomerella cingulata*, *Macrophoma commelinae*, *Micronectriella cucumeris*, *Mortierella isabellina*, *Mortierella ramanniana* var. *angulispora*, *Mucor tuberculisporus*, *Mucor inaeguisporus*, *Nannizzia gypsea* var. *incurvata*, *Penicillium chermesium*, *Penicillium expansum*, *Phialophora fastigiata*, *Rhizopus niveus*, *Rhizopus oryzae*, *Sclerotinia sclerotiorum*, *Sclerotium delphinii*, *Streptomyces cacaoi* subsp. *asoensis* and *Streptomyces* sp.

5. The process of claim 1, wherein absolute configuration of said produced optically active 3-hydroxypentanenitrile is S-configuration and said enzyme is an enzyme present in a cell, a culture solution or a treated substance thereof or a purified enzyme obtained from a microorganism selected from the group consisting of *Candida* genus, *Dipodascus* genus, *Geotrichum* genus, *Hyphopichia* genus, *Kluyveromyces* genus, *Pichia* genus, *Schizoblastosporion* genus, *Schwanniomyces* genus, *Brevundimonas* genus, *Paenibacillus* genus, *Rhodotorula* genus, *Pseudomonas* genus and *Streptomyces* genus.

6. The process of claim 1, wherein absolute configuration of said produced optically active 3-hydroxypentanenitrile is S-configuration and said enzyme is an enzyme present in a cell, a culture solution or a treated substance thereof or a purified enzyme obtained from a microorganism selected from the group consisting of *Candida albicans*, *Candida haemulonii*, *Candida intermedia*, *Candida maltosa*, *Candida mogii*, *Candida oleophila*, *Dipodascus ovetensis*, *Dipodascus tetrasperma*, *Geotrichum fragrans*, *Hypopichia burtonii*, *Kluyveromyces polysporus*, *Pichia stipitis*, *Schizoblastosporion kobayasii*, *Schwanniomyces occidentalis* var. *occidentalis*, *Brevundimonas diminuta*, *Paenibacillus alvei*, *Rhodotorula glutinis* var. *dairenensis*, *Pseudomonas stutzeri*, *Pseudomonas mendocina*, *Streptomyces coelescens* and *Streptomyces hydrogenans*.

7. The process of claim 1 wherein the reaction mixture further includes (NAD$^+$) and/or (NADP$^+$).

* * * * *